US006447788B1

(12) United States Patent
Strathausen

(10) Patent No.: US 6,447,788 B1
(45) Date of Patent: Sep. 10, 2002

(54) HONEY HERB BATH SOLUTION

(76) Inventor: Gerold Strathausen, Am Südhang 5, 84079 Bruckberg (DE)

( * ) Notice: Subject to any disclaimer, the term of this patent is extended or adjusted under 35 U.S.C. 154(b) by 0 days.

(21) Appl. No.: 09/367,864

(22) PCT Filed: Mar. 3, 1998

(86) PCT No.: PCT/DE98/00605

§ 371 (c)(1),
(2), (4) Date: Dec. 2, 1999

(87) PCT Pub. No.: WO98/38968

PCT Pub. Date: Sep. 11, 1998

(30) Foreign Application Priority Data

Mar. 3, 1997 (DE) .......................................... 197 08 478

(51) Int. Cl.⁷ .............................. A61K 7/00; A61K 7/48
(52) U.S. Cl. ...................... 424/401; 428/70.24; 428/74; 428/405; 428/745; 428/764; 428/770
(58) Field of Search ................................. 424/401, 405, 424/70.24, 74, 195.1, 745, 764, 770

(56) References Cited

U.S. PATENT DOCUMENTS 4,839,168 A * 6/1989 Abe et al.

OTHER PUBLICATIONS

Database Derwent on East, AN 1986–234111, FR 2576212 A, Simard, J.P., abstract, Jul. 1986.*
Database Derwent on East, AN1987–292526, DE 1617532 A, Heinforfer, F.K., abstract, Apr. 1971.*
Database Derwent on East, AN 1998–207871, CH 688787 A5, Linsig et al., abstract, Mar. 1998.*
Database Derwent on East, AN 1984–220669, US 4839168 A, Abe et al., abstract, Jun. 1989.*

* cited by examiner

Primary Examiner—Russell Travers
Assistant Examiner—Alysia Berman
(74) Attorney, Agent, or Firm—Brezina & Ehrlich

(57) ABSTRACT

A cosmetic body-care preparation, in particular a preparation for bathing, showering and/or for hair care or shampooing the hair. The composition contains honey in a proportion of at least 20% by weight.

14 Claims, No Drawings

HONEY HERB BATH SOLUTION

This application is a 371 of PCT/DE98/00605, filed Mar. 3, 1998.

BACKGROUND OF THE INVENTION

The invention relates to a cosmetic body-care preparation, in particular in the form of a cosmetic preparation for bathing, showering and/or for hair care or shampooing the hair, and a process for producing it.

This cosmetic body-care preparation is intended to be used as a full body bath, as a partial body bath, as a shower bath and/or as a hair care or shampoo product.

Conventional bath additives or similar body-care products often contain the most diverse chemical excipients, which are not always innocuous. For example, they can cause allergies, eczemas or inflammations. Anti-acid substances, for example soaps, can attack the natural acid protection coat of the skin, or even destroy it.

SUMMARY OF THE INVENTION

The object of the invention is based on providing a cosmetic body-care preparation, in particular as a cosmetic preparation for bathing, showering and/or for hair care or shampooing the hair, and a process for producing it, which essentially contains only natural ingredients, but no chemical preservation products, emulsifiers, binders, perfumes or other chemical excipients and which under normal circumstances has a shelf life without any time limits, i.e. which does not become unmixed.

In regard to the cosmetic body-care preparation, this object is attained in the use of a composition containing at least 20% by weight of honey.

DETAILED DESCRIPTION OF THE INVENTION

The cosmetic body-care preparation in accordance with the invention in particular to be used for bathing, showering and/or for hair care or shampooing, is distinguished in that it contains honey in a proportion of at least 20% of its total weight. In accordance with a particularly preferred embodiment, the cosmetic body-care preparation of the invention contains a proportion of honey of 40 to 60% of its total weight, preferably 50% of its total weight.

The solution of the technical problems mentioned above was only successful after prolonged and extensive test runs.

Honey, in particular mixed honey from the woods in its various compositions occurring in Central Europe and other countries, has an antibacterial and germ-reducing, i.e. a healing, grooming and protective effect. This per se has been long known. Even though these positive effects of the honey can be detected when highly diluted, a noticeable effect only occurs at a high dosage. Commercially available bath additives, however, contain no more than 2% of honey. Bath additives containing essential oils or herbal extracts are also offered, since their health-promoting effects are also known. Moreover, surfactants used as washing agents or bath additives are also known.

However, up to now no body-care preparation of the type of the invention, which contains honey, in particular honey from the woods or mixed honey from the woods at high concentrations, and furthermore natural essential oils and herbal extracts and combines these with an active washing surfactant, is available anywhere in the world. Not the least reason for this lies in the extraordinarily poor miscibility of essential oils and herbal extracts, in particular herbal extracts in alcohol. The miscibility of honey and surfactants, or of surfactants and essential oils, is less problematic. But it is more difficult to mix the last mentioned materials with essential oils and herbal extracts. In accordance with a galenic point of view, the unmixing of the individual components must surely be expected, so that a certain prejudice against such a cosmetic body-care preparation would also exist in the technical field.

By means of the invention it has been achieved to make a honey-herbal body-care preparation available which contains only natural components. No manner of preservation agents, emulsifiers, binders, perfumes or other chemical excipients, or even only water, are required as additives. Under normal conditions, the novel honey-herbal body-care preparation has a shelf life without any time limits, i.e. it does not become unmixed.

In accordance with a preferred basic formula of the invention, the body-care preparation contains the following components in weight-%:

Honey, 40 to 60%

Surfactants, 40 to 60%

Naturally pure essential oils, 1 to 5%

Herbal extracts in alcohol, 0.1 to 1%.

In a preferred body-care preparation, the surfactant is sodium lauryl ether sulfate. The proportion of the surfactants or the surfactant can advantageously be approximately 48%.

The proportion of the naturally pure essential oils is usefully approximately 1.7%. In this case, the naturally pure essential oils can be combined in a mixture as follows:

Oleum Rosmarini, 28 to 31%

Oleum Lavendulae, 22 to 25%

Oleum Mellisae, 22 to 25%

Oleum Pini pum., 22 to 25%

(Total: 100%).

The proportion of naturally pure essential oils in the total compound therefore is:

Oleum Rosmarini, 0.5%

Oleum Lavendulae, 0.4%

Oleum Mellisae, 0.4%

Oleum Pini pum., 0.4%.

Furthermore, in connection with a particularly preferred embodiment, the proportion of the herbal extracts in alcohol can be 0.3%. The herbal extracts in alcohol can be preferably composed of the following mixture:

Extractum Arnicae, 32 to 35%

Extractum Calendulae, 64 to 70%

(Total: 100%).

Thus, the proportion of the herbal extracts in alcohol in the total compound is:

Extractum Arnicae, 0.1%

Extractum Calendulae, 0.2%.

The advantageous properties of the basic components will be described in what follows:

The Honey

It is particularly advantageous if the honey is a mixed honey from the woods of native or Central European coniferous trees, which also contains acacia honey. This honey contains numerous nourishing, grooming and healing ingredients, and is at the same time used as a preservation material.

Honey from mixed woods has the highest proportion of inhibitors of all types of honey. These are agents which inhibit the growth of bacteria. The content of organic acids of the honey is almost identical to that of the acid content of the human skin. An optimal protection of the acid protection coat of the human skin is provided by means of this. Moreover, it contains vitamin C, B1, B2, B6, E, folic acid, biotine-H and niacin PP. Mg, $SiO_2$, P, S, Mn, Si, K, Na, Ca, Cu and Fe are contained in it as trace elements. The honey to be used in accordance with the invention also contains a number of amino acids, namely leucine, asparagine, glutamic acid, phenylalanine, threonine, arginine, histidine, glycine, lysine, serine, valine, cystine and proline. Besides the natural growth hormone acetylcholine, more than 50 natural aromatics are contained in the honeys, among them isobutyl aldehyde and acetaldehyde, acetone and biacetyl.

The Naturally Pure Essential Oils

In comparison with commercially available bath additives, the cosmetic body-care preparation contains a very high proportion of natural essential oils. They have a fresh scent, of course, but evaporate and in this way get into the body via the respiratory system. A pleasant body odor is achieved in this way and at the same time a health-promoting aroma therapy. The Oleum Rosmarini (oil of rosemary) promotes the circulation to the heart and is vitalizing. The Oleum Lavendulae (oil of lavender) has cramp-relieving, calming, strengthening and disinfecting properties. The Oleum Melissae (balm mint oil) also has a calming, relaxing, stress-relieving and quieting effect. The Oleum Pinipum (mountain pine oil) also has a relaxing effect. But it also relieves illnesses of the respiratory system and colds.

The Herbal Extracts in Alcohol

Extractum Arnicae fluid (30%) 1:1 (extract of the flower of Arnica montana) and Extractum Calendulae fluid (35%) 1:2 (marigold flower extract) are used as herbal extracts in alcohol. These extracts calm and relax the epidermis, which is damaged by outside effects, in an excellent way. The connective tissue is strengthened, the flow of blood is promoted and infections are relieved, sometimes even cured.

The Surfactants

Among the surfactants, sodium lauryl ether sulfate is a particularly useful and mild washing substance. However, the employment of another, similarly mild surfactant is also possible. The dirt, which has a daily effect on the skin, and the metabolic products of the skin as an organ must be removed as gently as possible in order to assure access to the skin surface for the effective ingredients of the cosmetic body-care preparation.

Based on all these positive properties of the cosmetic body-care preparation of the invention, its use offers excellent protection for the skin against the damaging effects of pollution. It offers a clearly noticeable relief of the skin damage caused by it. The cosmetic body-care preparation can be used already for babies and children. Its medical application is recommended in connection with the following skin disorders:

scaling of the skin, in particular dandruff, eczemas of the head, eczemas of the body, in particular of the bacterial type, acne, aiding the treatment of -eurodermatitis, psoriasis, herpes and itching, inflammation of the mucous membranes, in particular in the anal and genital areas.

A particularly preferred composition of the cosmetic body-care preparation in accordance with the invention consists of (in weight-%):

| | |
|---|---|
| Mixed honey from the woods | 50.0% |
| Sodium lauryl ether sulfate | 48.0% |
| Oleum Rosmarini | 0.5% |
| Oleum Lavendulae | 0.4% |
| Oleum Melissae | 0.4% |
| Oleum Pini pum. | 0.4% |
| Extractum Arnicae | 0.1% |
| Extractum Calendulae | 0.2% |
| | (a total of 100.0%) |

The production of a 10 kg batch of such a cosmetic body-care preparation will now be described. It is of course possible to prepare larger batches, as long as the requirements as to apparatus are met.

Initially, 5 kg of mixed honey from the woods will be gently heated to 30 to 31° C. in a water bath or similarly operating heat exchanger. Under no circumstances should temperatures above 40° C. occur on the wall of the vessel during heating, because otherwise the quality of the honey would suffer in an impermissible way. Thereafter, the honey is allowed to slowly cool to the room temperature of 21 to 22° C. or, if the room temperature lies below or above, it is cooled to this temperature. Then the agitator is operated. This can be a conventional agitator, such as is used by do-it-yourselfers for mixing of latex paints, for example. The speed of rotation of the agitator is set to 2000 to 2400 $min^{-1}$.

Now the essential oils are added separately and in the following sequence:

40 g Oleum Pini pum., 40 g Oleum Lavendulae 40 g Oleum Melissae, and 50 g Oleum Rosmarini.

Each oleum is stirred in or admixed for approximately 2 to 5 min. before the next one follows.

The extracts in alcohol, namely 10 g Extractum Arnicae and 20 g Extractum Calendulae are initially separately mixed for 2 to 4 min. and are then stirred into or admixed with the mixture of mixed honey from the woods and essential oils.

Lastly, 4.8 kg of sodium lauryl ether sulfate is stirred into or admixed with this mixture. From its composition, this mixture is the finished cosmetic body-care preparation. It then must rest at 20 to 21° C., protected from light and covered, but not sealed, for approximately 30 to 40 hours. Possibly mixed-in air can escape in this way.

The last step is the decanting of the honey-herb body-care product into containers customary in commerce, by hand for the 10 kg batch described here, otherwise in a conventional decanting installation.

What is claimed is:

1. A cosmetic body-care preparation, consisting essentially of:

about 40–60% by weight of at least one surfactant;

about 1–5% by weight of at least one essential oil; and about 0.1–1% by weight of at least one alcoholic herbal extract and the hemaindes honey.

2. The body-care preparation in accordance with claim 1, wherein the honey is present in an amount of about 50% by weight.

3. The body-care preparation in accordance with claim 1, wherein the at least one essential oil comprises, by weight:

Rosemary oil, 28 to 31%;

Lavender oil, 22 to 25%;

Balm mint oil, 22 to 25%; and

Mountain pine oil, 22 to 25%.

4. The body-care preparation in accordance with claim 1, wherein the at least one alcoholic herbal extract comprises, by weight:

Arnica extract, 32 to 35%; and

Marigold extract, 64 to 70%.

5. The body-care preparation in accordance with claim 1, wherein the honey comprises acacia honey, honey from Central-European coniferous trees, or a mixture thereof.

6. The body-care preparation in accordance with claim 1, in the form of a preparation for bathing, showering or hair care.

7. The body-care preparation in accordance with claim 1, wherein the honey is present in an amount of about 50% by weight, and the at least one surfactant is present in an amount of about 48% by weight.

8. A process for preparing a cosmetic body-care preparation, comprising the steps of:

indirectly heating honey with a heat exchange fluid to 30 to 31° C. and cooling the heated honey to substantially room temperature;

at room temperature, adding at least one essential oil to the cooled honey, each said essential oil added to the honey being added individually and in sequence, each said adding being followed by mixing for about 2 to 5 min;

forming a mixture containing at least one alcoholic herbal extract;

at room temperature, stirring the mixture of herbal extracts into the honey to which the at least one essential oil has been added; and at room temperature, mixing at least one surfactant with the honey to which the at least one essential oil and at least one herbal extract have been added, to form the preparation.

9. The process in accordance with claim 8, wherein the at least one herbal extract comprises at least two herbal extracts which are mixed together, followed by stirring for about 2 to 4 minutes.

10. The process in accordance with claim 8, additionally comprising covering without sealing the preparation, protecting the covered preparation from light, and permitting the protected and covered preparation to rest at substantially room temperature for 30 to 40 hours, so that any air in the preparation can escape.

11. The process in accordance with claim 8, wherein the following essential oils are sequentially added:

Mountain pine oil;

Lavender oil;

Balm mint oil; and

Rosemary oil.

12. The process in accordance with claim 8, wherein room temperature is about 21–22° C.

13. The process in accordance with claim 8, wherein the heating takes place in a water bath.

14. The process in accordance with claim 8, wherein the heating takes place with the honey coming into indirect heat exchange contact with the fluid at a temperature of no more than about 40° C.

* * * * *